(12) United States Patent
Vanoppen et al.

(10) Patent No.: US 7,595,424 B2
(45) Date of Patent: Sep. 29, 2009

(54) METHOD FOR PRODUCING AROMATIC AMINES OR ALIPHATIC AMINO ALCOHOLS

(75) Inventors: Dominic Vanoppen, Schifferstadt (DE); Frederik Van Laar, Limburgerhof (DE); Thomas Beuermann, Mannheim (DE); Georg Krug, Moerlenbach (DE); Steffen Oehlenschlaeger, Ludwigshafen (DE); Ekkehard Schwab, Neustadt (DE); Hartwig Voss, Frankenthal (DE); Konrad Morgenschweis, Dresden (DE); Ulrich Penzel, Tettau (DE); Dietrich Tittelbach-Helmrich, Tauscha (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/816,658

(22) PCT Filed: Feb. 22, 2006

(86) PCT No.: PCT/EP2006/060174

§ 371 (c)(1),
(2), (4) Date: Aug. 20, 2007

(87) PCT Pub. No.: WO2006/089906

PCT Pub. Date: Aug. 31, 2006

(65) Prior Publication Data

US 2008/0146848 A1 Jun. 19, 2008

(30) Foreign Application Priority Data

Feb. 23, 2005 (DE) .................... 10 2005 008 613

(51) Int. Cl.
*C07C 209/36* (2006.01)

(52) U.S. Cl. ........................ 564/420; 564/422
(58) Field of Classification Search .......... 564/420, 564/422
See application file for complete search history.

(56) References Cited

U.S. PATENT DOCUMENTS

| 5,563,296 | A  | * | 10/1996 | Zarnack et al. | 564/422 |
| 6,350,911 | B1 | * | 2/2002  | Sander et al.  | 564/305 |
| 6,423,872 | B2 | * | 7/2002  | Marion         | 564/422 |
| 6,537,500 | B1 | * | 3/2003  | Brenner et al. | 422/88  |
| 7,091,383 | B2 | * | 8/2006  | Vanoppen et al.| 564/422 |

FOREIGN PATENT DOCUMENTS

| DE | 2 044 657   | 3/1972  |
| EP | 0 634 391   | 1/1995  |
| EP | 0 971 225   | 1/2000  |
| EP | 0 978 505   | 2/2000  |
| EP | 1 138665    | 7/2004  |
| JP | 2003261530  | 9/2003  |
| WO | 00 35852    | 6/2000  |
| WO | 02 088860   | 11/2002 |
| WO | 03 066571   | 8/2003  |

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

The invention relates to a process for preparing aromatic amines by hydrogenation of nitroaromatics in the presence of catalysts, in which a fluid reaction mixture which comprises amines and from which the catalysts are separated off is formed in a reactor. After the catalysts have been separated off, a measurement of the absorption of UV/VIS radiation by the reaction mixture is carried out to determine the concentration of nitro and nitroso compounds in the reaction mixture.

13 Claims, 4 Drawing Sheets

METHOD FOR PRODUCING AROMATIC AMINES OR ALIPHATIC AMINO ALCOHOLS

Figure 1:
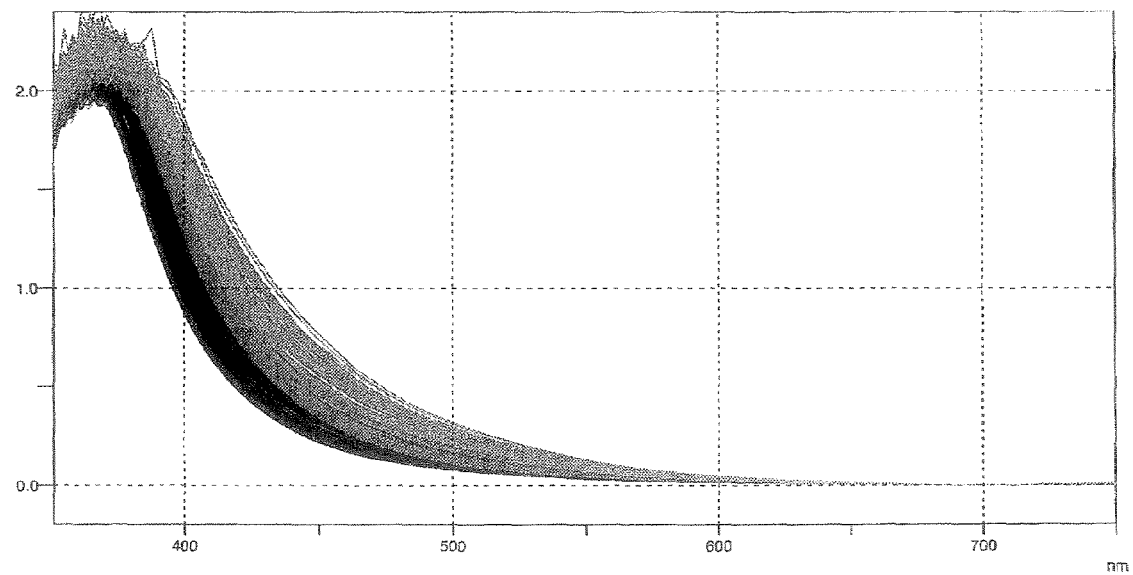

The invention relates to a process for the preparation of aromatic amines by hydrogenation of nitroaromatics or of aliphatic amino alcohols by hydrogenation of nitro alcohols in the presence of catalysts.

The preparation of amines, in particular aromatic monoamines or polyamines by catalytic hydrogenation of mononitro and/or polynitro compounds, is known from the prior art.

DE-A 2 044 657 relates, for example, to a process for preparing tolylenediamine by hydrogenation of dinitrotoluene in the presence of hydrogenation catalysts comprising nickel or ruthenium.

EP-B1 1 138 665 relates to a process for the catalytic hydrogenation of aromatic nitro compounds, in which the hydrogenation is carried out continuously using a catalyst which comprises at least nickel and, if appropriate, aluminum. After the hydrogenation has been carried out, the catalyst is separated from the reaction mixture in a separation zone.

The document EP-B1 0 978 505 describes a process for the hydrogenation of a nitroaromatic composition by contacting the nitroaromatic composition with hydrogen in a reactor using a monolithic catalyst. After the hydrogenation has been carried out, the hydrogenated reaction product, which comprises unreacted dinitrotoluene, water and toluenediamine, is continuously removed from the reactor. Further documents of the prior art which describe processes for preparing amines by hydrogenation of nitro compounds are, for example, EP-A 634 391 or WO 00/35852.

The reaction mixture obtained on carrying out the hydrogenation of nitroaromatics in a reactor comprises not only the aromatic amines but also nitro and nitroso compounds which comprise, for example, the nitroaromatics used as starting materials or intermediates formed in the reactor. Nitro and nitroso compounds can decompose explosively, in particular on heating. For safety reasons, monitoring of the reaction mixture with regard to the concentration of nitro and nitroso compounds present therein is therefore important. The safety risk increases with increasing reactor size and decreasing residence times in the reactor. It has to be ensured that these explosive compounds are reacted completely in the reactor before the reaction mixture is passed to, for example, a subsequent distillation.

A further problem which arises in the catalytic hydrogenation of nitroaromatics is that the catalysts become deactivated over time. The lower the activity of the catalysts, the lower the proportion of the starting materials converted into amines, so that the proportion of unreacted nitroaromatics remaining in the reactor increases. Monitoring of the catalyst activity is therefore necessary, in particular to enable a sufficient amount of unexhausted catalyst to be introduced into the reactor.

In the prior art, the concentration of nitro and nitroso compounds and the activity of the catalyst is monitored with the aid of gas chromatography samples (for example in the process according to WO 03/066571 A1).

It was an object of the invention to provide a process for preparing aromatic amines by hydrogenation of nitroaromatics in the presence of catalysts in a reactor, which allows simple on-line monitoring of the concentration of nitro and nitroso compounds in a reaction mixture comprised in the reactor. A further object was to make possible on-line monitoring of the catalyst activity in the reactor.

This object is achieved according to the invention by a process for the preparation of aromatic amines by hydrogenation of nitroaromatics or of aliphatic amino alcohols by hydrogenation of nitro alcohols in the presence of catalysts, in which a fluid reaction mixture which comprises amines or amino alcohols and from which the catalysts are separated off is formed in a reactor. After the catalysts have been separated off, a measurement of the absorption of UV/VIS radiation by the reaction mixture is carried out to determine the concentration of nitro and nitroso compounds in the reaction mixture.

In this context, nitro compounds are organic compounds in which a hydrogen atom has been replaced by a nitro group ($NO_2$ group). Nitroso compounds are organic compounds comprising a nitroso group (NO group) bound to an aromatic carbon atom. Amines are monoamines, diamines and polyamines. The fluid reaction mixture can be either liquid or gaseous.

UV/VIS radiation is electromagnetic radiation in the visible or UV region. Measurement of the absorption of UV VIS radiation by the reaction mixture allows the concentration of nitro and nitroso compounds in the reaction mixture to be determined. When monochromatic UV/VIS radiation having an initial intensity $I_0$ passes through a dilute solution of an absorbing substance (for example the reaction mixture) having a thickness d, the Lambert-Beer law describes the absorption of the radiation by the solution. The Lambert-Beer law states that:

$$2.3 \cdot \log \frac{I_0}{I} = A = \varepsilon \cdot d \cdot c$$

where
$I_0$: intensity of the radiation before entry into the solution
I: intensity of the radiation after passing through the path length d
d: path length (for example cuvette dimension) through the fluid (e.g. the solution) in cm
c: concentration of the absorbing substance in mol/l
$\varepsilon$: molar extinction coefficient in l/(mol×cm) (material constant)
A: absorbance.

There is a linear relationship between the concentration of the fluid and the absorbance. The concentration of an absorbing sample can in this way be determined by a measurement of the absorbance (for example by means of a spectrophotometer) with the aid of a calibration curve or known extinction coefficients (photometry).

The removal of the catalysts from the reaction mixture prior to the absorption determination simplifies the work-up of the end product in the process of the invention. Furthermore, the reaction mixture has to be largely freed of the black catalyst particles for the absorption measurements since these interfere in UV/VIS spectroscopy.

To determine the concentration of the nitro and nitroso compounds, an absorption spectrum in a wavelength range of the UV/VIS radiation or the absorption (absorbance) of UV/VIS radiation having a single wavelength can be measured. The measurement is preferably carried out monochromatically (using radiation having a selected wavelength). This is entirely sufficient to determine the concentration of the nitro and nitroso compounds in the reaction mixture. The wavelength of the radiation is selected so that contributions of other components of the reaction mixture, in particular amines, to the absorption of the radiation are very small.

The measurement of the absorption spectrum in a wavelength range of UV/VIS radiation has the advantage that erroneous measurements, which can be caused, for example, by gas bubbles in the reaction mixture, are readily recognized and not employed for determination of the concentration. However, such a measurement of an absorption spectrum requires a more expensive photometer in which both the light source comprised therein and the detector have to cover such a wavelength range.

In a preferred embodiment of the present invention, a measurement of the absorption of UV/VIS radiation by the reaction mixture is additionally carried out in another wavelength range or at another wavelength to correct the baseline. Such a baseline correction is necessary to compensate for intensity fluctuations of the light source emitting the UV/VIS radiation. The wavelength range or the wavelength are for this purpose selected so that the nitro and nitroso compounds make no contribution or a negligibly small contribution to the measured absorption by the reaction mixture in this wavelength range or at this wavelength. This measurement gives a correction value. The determination of the concentration of the nitro and nitroso compounds is carried out in a wavelength range or at a wavelength in/at which it is essentially the nitro and nitroso compounds in the reaction mixture which absorb the UV/VIS radiation. The measured absorption is then corrected by the correction value which was measured in the other wavelength range/at the other wavelength for the baseline correction. The measurement of the absorption by the nitro and nitroso compounds and the correction values can be carried out simultaneously by means of two photometers set to different wavelength ranges. However, a spectrum comprising both wavelength ranges can also be recorded by means of one photometer or measurements at the two different wavelengths can be carried out alternately.

In the present invention, the catalysts are separated off from the reaction mixture by means of at least one separation process selected from the group consisting of membrane filtration, sedimentation and centrifugation or by means of any other method known from the prior art. The removal of a catalyst comprised in a reaction mixture is known, for example, from DE-A1 3245 318, DE A13040 631 or WO 03/066571. A combination of separation processes (for example sedimentation and subsequent membrane filtration) is also possible in order to achieve very complete removal of the catalyst from the reaction mixture before absorption measurements are carried out.

The measurement of the absorption of UV/VIS radiation in the present invention can also be carried out at a pressure above ambient pressure and/or at ambient pressure. For example, a photometer can be located in a region behind a membrane filter for removal of the catalyst, in which the filtrate leaving the filter is under a pressure above ambient pressure. However, the absorption measurement can also be carried out in a region of an apparatus for preparing aromatic amines, in which the catalyst has already been separated off and the reaction mixture has been depressurized to ambient pressure.

In the present invention, the measurement of the absorption of UV/VIS radiation by the reaction mixture can be carried out in a main stream taken from the reactor or preferably in a substream branched off from the main stream.

In a preferred embodiment of the present invention, an amount of nitroaromatics, nitro alcohols or catalysts introduced into the reactor is regulated as a function of the determination of the concentration of the nitro and/or nitroso compounds in the reaction mixture. The present invention therefore also provides a regulating method which regulates the amount of catalyst and or nitroaromatics or nitro alcohols introduced into the reactor in the preparation of aromatic amines by hydrogenation of nitroaromatics or of aliphatic amino alcohols by hydrogenation of nitro alcohols in the presence of catalysts in a reactor as a function of a concentration, determined by measurement of the absorption, of nitro and/or nitroso compounds in the reaction mixture. The measured concentration of nitro and/or nitroso compounds in the reaction mixture increases when the activity of the catalyst present in the reactor decreases. In this case, the amount of nitroaromatics or nitro alcohols added can be reduced or the amount of new active catalyst added can be increased.

The preparative process of the invention is preferably used to prepare aromatic amines by hydrogenation of nitroaromatics having one or more nitro groups and from 6 to 18 carbon atoms. The nitroaromatics are, for example, nitrobenzene, nitrobenzenes such as 1,2-, 1,3-, 1,4-dinitrobenzene, nitrotoluenes such as o-, m-, p-nitrotoluene, dinitrotoluenes such as 2,4-, 2,6-, 2,3-, 3,4-, 2,5-dinitrotoluene, 2,4,6-trinitrotoluene, nitroxylenes such as 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes such as 1-, 2-nitronaphthalene, 1,5- and 1,8-dinitronaphthalene, chloronitrobenzenes such as 2-chloro-1,3-, 1-chloro-2,4-dinitrobenzene, o-, m-, p-chloronitrobenzene, 1,2-dichloro-4-, 1,4-dichloro-2-, 2,4-dichloro-1- and 1,2-dichloro-3-nitrobenzene, chloronitrotoluenes such as 4-chloro-2-, 4-chloro-3-, 2-chloro-4- and 2-chloro-6-nitrotoluene, nitroanilines such as o-, m-, p-nitroaniline and also any mixtures of 2 or more of the nitro compounds mentioned. In addition, aliphatic amino alcohols can be prepared by hydrogenation of nitro alcohols using the process of the invention. The nitro alcohols are, for example, tri(hydroxymethyl)nitromethane, 2-nitro-2-methyl-, 2-nitro-2-ethyl-1,3-propanediol, 2-nitro-1-butanol and 2-nitro-2-methyl-1-propanol and also any mixtures of 2 or more of the nitro compounds mentioned.

Preference is given to hydrogenating dinitrotoluene, in particular 2,4-dinitrotoluene or its industrial mixtures with 2,6-dinitrotoluene, to form the corresponding amine by the process of the invention. In a particularly preferred embodiment of the present invention, toluenediamine is prepared by hydrogenation of dinitrotoluene and a measurement of the absorption of UV/VIS radiation is carried out to determine the concentration essentially of dinitrotoluene and aminonitrotoluene comprised in the reaction mixture. Aminonitrotoluene is an intermediate formed in the hydrogenation of dinitrotoluene. The measurement of the absorption by essentially dinitrotoluene and aminonitrotoluene in the reaction mixture is preferably carried out at a wavelength in the range from 450 to 550 nm, preferably at 500 nm, or an absorption spectrum is recorded in a wavelength range from 350 to 750 nm. In the range from 450 to 550 nm, the radiation is absorbed essentially by the dinitrotoluene and aminonitrotoluene comprised in the reaction mixture. The absorption by the toluenediamine and the water comprised in the reaction mixture is low in this wavelength range. Absorption measurements for baseline correction can be carried out in a wavelength range from 650 to 750 nm, preferably at 700 nm. In this wavelength range, the absorption by dinitrotoluene and aminonitrotoluene is virtually zero.

The invention further relates to an apparatus for carrying out the process of the invention, which comprises a reactor for the hydrogenation of nitroaromatics or of nitro alcohols in the presence of catalysts to form a reaction mixture, and a separation element for separating off the catalysts from the reaction mixture and a UV/VIS spectrometer for measuring the absorption of UV/VIS radiation by the reaction mixture to determine the concentration of nitro and nitroso compounds in the reaction mixture.

Reactors used are the customary and known hydrogenation reactors. Examples are stirred tanks, fluidized-bed reactors, monolithic, catalytic hydrogenation reactors as described, for example, in EP-A2 1310302, shell-and-tube reactors, bubble columns which may comprise packings, or loop reactors such as loop Venturi reactors or jet loop reactors having an internal and external circuit, as described, for example, in WO 00/35852 or WO 03/068724.

The separation element is, for example, a centrifuge or a filter, in particular a membrane filter. The UV/VIS spectrometer comprises a UV/VIS light source and a detector between which a vessel through which the reaction mixture can flow is located. The distance which the light emitted by the light source travels in the measurement of the absorption through the reaction mixture present in the vessel before it leaves the vessel again and is detected by the detector is the path length, which is preferably in the range from 0.5 to 1.5 cm. The light source and the detector are preferably mounted in a flow cell which is connected to the substream lines conveying reaction mixture.

The light source preferably radiates in a very wide spectral range (continuum radiator) if absorption spectra are to be recorded. For measurement of the absorption at a particular wavelength, a light source which radiates in a narrow spectral range, in particular a monochromatic light source, is also satisfactory. The light source can also comprise two different lamps in order to cover a wide spectrum. The light source preferably comprises a tungsten filament lamp, a hydrogen lamp or a deuterium lamp. A monochromator can be employed for splitting the light into individual wavelengths. The detector can comprise, for example, a vacuum photocell, a photomultiplier or a field of silicon photodiodes.

The signal detected by the detector is, if appropriate, amplified by an amplifier and evaluated in an evaluation unit (for example a computer). The result of the concentration of nitro and nitroso compounds determined from the measured absorption is, for example, displayed on a display for the information of a user. It can be employed for regulating the amine preparation process or can trigger an alarm signal if a particular nitro and nitroso compound concentration is exceeded. Furthermore, the evaluation unit can be programmed so that it recognizes and discards (i.e. does not display, does not use for regulating the process or does not take into account for any other purpose) a measurement which is erroneous as a result of gas bubbles in the reaction mixture.

The apparatus of the invention makes possible automatic on-line measurement of the concentration of the nitro and nitroso compounds in the reaction mixture.

The above-described regulating method based on the concentration measurement enables, in an advantageous fashion, the catalyst consumption to be optimized and thus reduced.

The invention is illustrated below with the aid of the example and the drawing.

Figure 2:
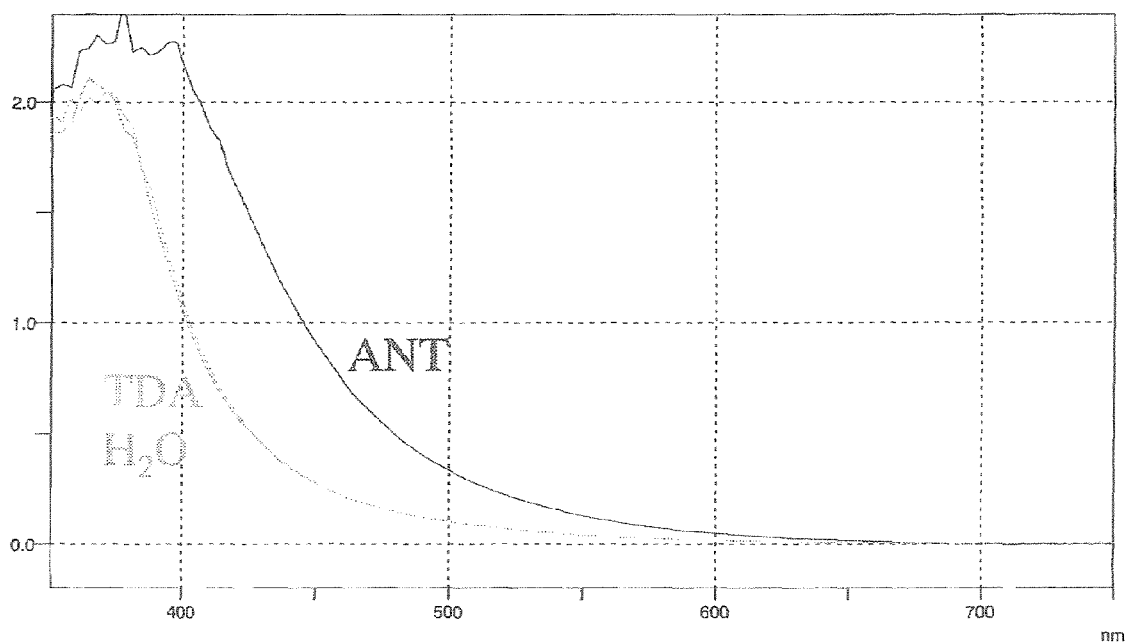
Figure 3:
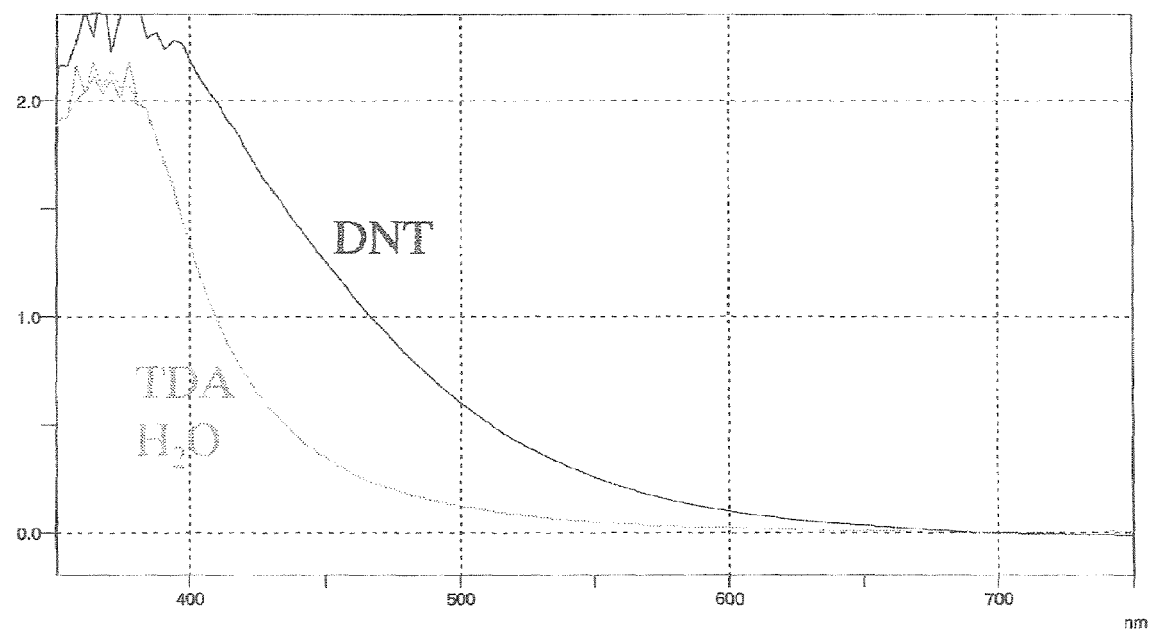
Figure 4:
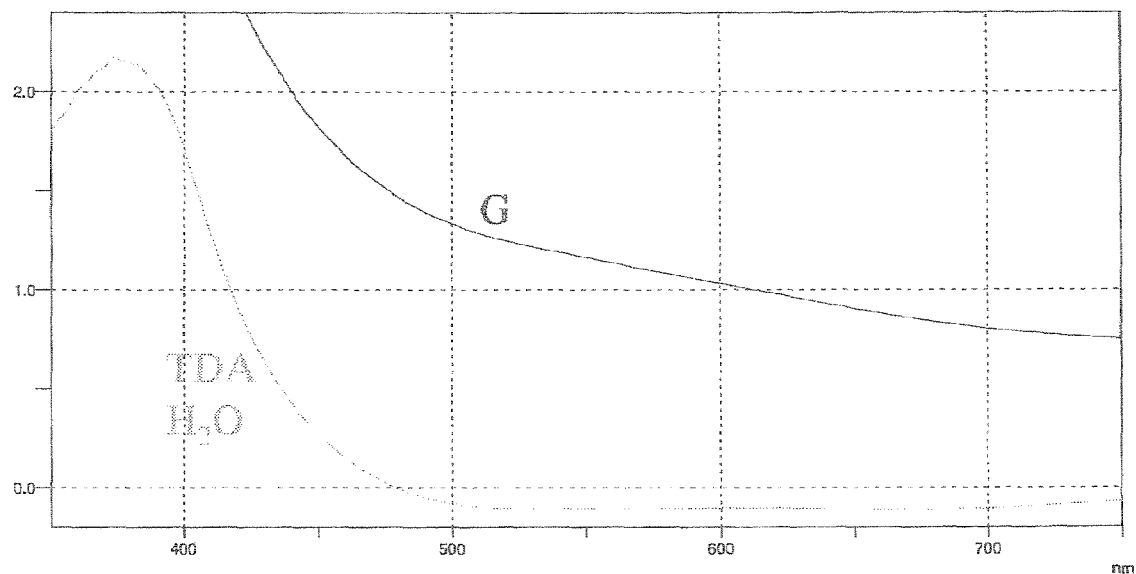
Figure 5:
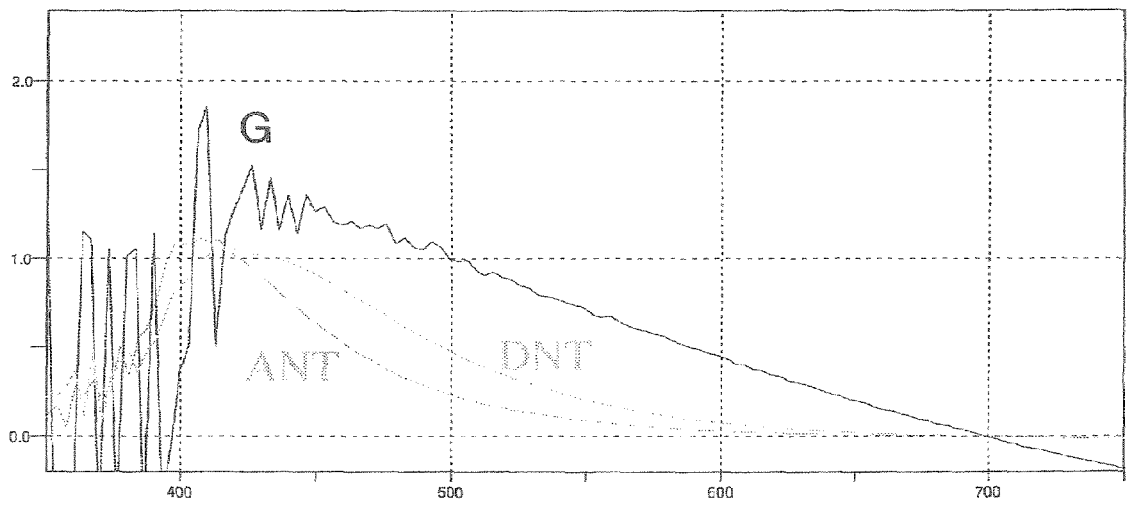
Figure 6:
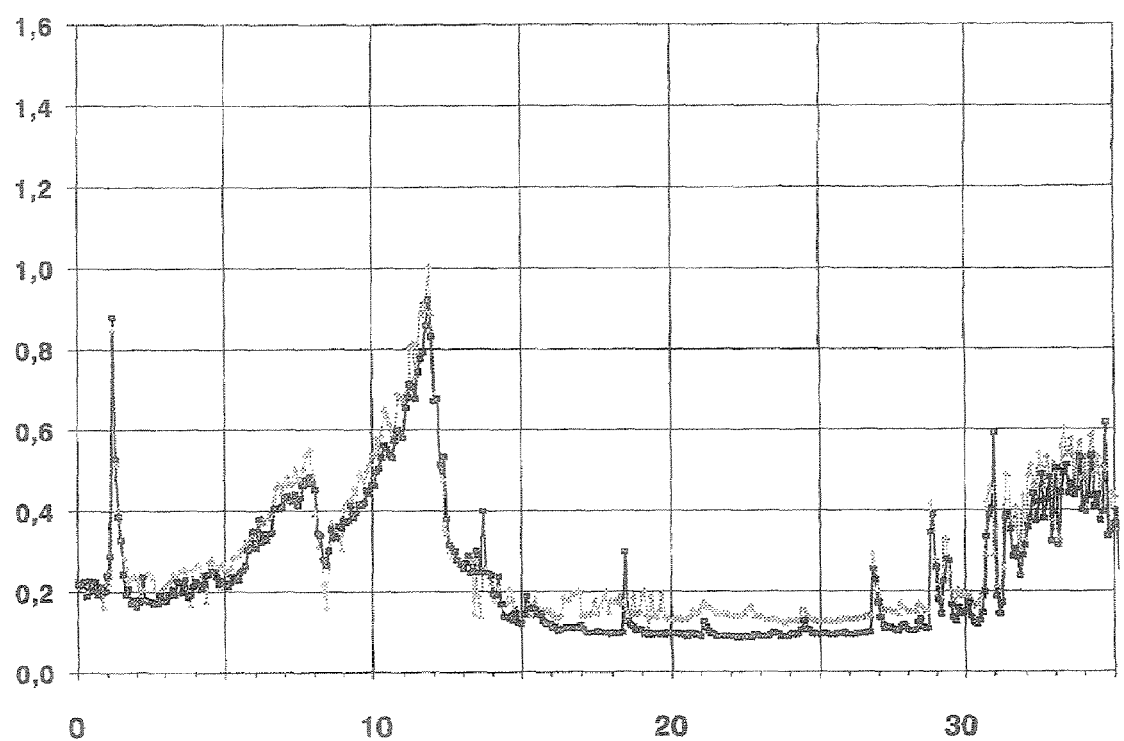

In the drawing:

FIG. 1 shows a UV/VIS absorption spectrum recorded on a solution of amino-nitrotoluene and dinitrotoluene in a toluenediamine/$H_2O$ matrix, FIG. 2 shows a UV/VIS absorption spectrum of a solution of 200 ppm of aminonitrotoluene in a toluenediamine/$H_2O$ matrix, FIG. 3 shows a UV/VIS absorption spectrum of a solution of 350 ppm of dinitrotoluene in a toluenediamine $H_2O$ matrix, FIG. 4 shows a UV/VIS absorption spectrum of a reaction mixture having a TDA/$H_2O$ matrix which has been influenced by a gas bubble, FIG. 5 shows a comparison of aminonitrotoluene and dinitrotoluene absorption spectra with a spectrum influenced by a gas bubble and FIG. 6 shows the concentration monitoring of a pilot reactor in the hydrogenation of dinitrotoluene by measurement of the absorption of UV/VIS radiation by the reaction mixture.

The figures will be described in more detail for the hydrogenation of dinitrotoluene in example 1.

EXAMPLE 1

In a 5 l pilot reactor, dinitrotoluene was hydrogenated over a supported nickel catalyst having a mean particle size of from 5 to 10 µm at a pressure of from 20 to 25 bar and a temperature of from 120 to 125° C. The concentration essentially of dinitrotoluene and aminonitrotoluene in the reaction mixture was determined by absorption measurements. For this purpose, quartz window cells were installed beyond a membrane filter and, downstream thereof, beyond a control valve in a region under ambient pressure. The path length in both cells was 1 cm. The cells were connected using optical fiber cables to a UV/VIS spectrometer equipped with a diode field detector.

To calibrate the method, a small stream of a solution having a known concentration of dinitrotoluene and aminonitrotoluene was pumped by means of an HPLC pump into the reaction mixture stream flowing out of the reactor. An absorption spectrum was recorded every minute during operation of the plant and this was evaluated by means of a computer and stored on a hard disk. The computer program also carried out a baseline correction of the recorded spectra.

Evaluation of the spectra recorded in this way showed that 700 nm is a suitable wavelength for the absorption measurement for the baseline correction. A wavelength of 500 nm was chosen as wavelength for determination of the concentration of nitro and nitroso compounds.

FIG. 1 shows a UV/VIS absorption spectrum recorded on a solution of aminonitrotoluene and dinitrotoluene in a toluenediamine/$H_2O$ matrix. The spectra have been baseline-corrected. The absorption (absorbance) in absorption units is plotted on the Y axis and the wavelength in nm is plotted on the X axis. The spectra display a maximum at about 375 nm. As a result of the baseline correction, the absorption is 0 in the region of 700 nm. At 500 nm, the absorption is significantly above 0. The various spectra differ because the solutions examined have different nitro group concentrations.

FIG. 2 shows a UV/VIS absorption spectrum of a solution of 200 ppm of amino-nitrotoluene in a toluenediamine/$H_2O$ matrix. This is 200 ppm of 4-amino-2-nitrotoluene. Once again, the absorption (absorbance) is plotted on the Y axis and the wavelength is plotted on the X axis. A baseline correction was carried out. The two curves labeled as TDA/$H_2O$ represent two spectra of the toluenediamine $H_2O$ matrix alone. The curve labeled ANT is the absorption spectrum of aminonitrotoluene in the toluenediamine/$H_2O$ matrix.

At a wavelength of 500 nm, the major part of the absorbed light is absorbed by the aminonitrotoluene.

FIG. 3 shows a UV/VIS absorption spectrum of a solution of 350 ppm of dinitrotoluene in a toluenediamine/$H_2O$ matrix. The absorption (absorbance) is plotted on the Y axis and the wavelength of the UV/VIS radiation is plotted on the X axis. A baseline correction was carried out. The two curves labeled as TDA/$H_2O$ once again represent two spectra of the toluenediamine/$H_2O$ matrix alone. The curve labeled DNT represents the absorption spectrum of dinitrotoluene in the toluenediamine/$H_2O$ matrix. At a wavelength of 500 nm, the major part of the absorbed light is once again absorbed by the dinitrotoluene.

To determine a calibration curve, the concentrations were varied between 50 and 1000 ppm. These concentrations were remeasured by gas chromatography. For both substances, viz. both aminonitrotoluene and dinitrotoluene, a gradient of the calibration curves of about 800 ppm per absorption unit was determined at a wavelength of the UV/VIS radiation employed.

At a wavelength of 500 nm, the absorption of the toluenediamine/$H_2O$ matrix is about 0.1 (+/−0.05). This gives a detection limit of 40-50 ppm. However, lower detection limits can be achieved, e.g. by measurement of the absorption using greater path lengths of the solution.

Furthermore, the influence of gas bubbles on the result of the absorption measurement was checked. At a hydrogen concentration in the reactor in the region of saturation, small gas bubbles can form as a result of the pressure drop over the membrane filter. These can influence the spectroscopic results by scattering the UV/VIS radiation. However, this represents only a small problem. Particularly when the measurement cell was arranged vertically so that the reaction mixture flowed upward, no deviating spectra were obtained in normal operation. In the second measurement cell in the region under ambient pressure, a large gas bubble formed every now and again, caused in particular by changes in the operating state. This gave spectra as shown in FIG. 4.

FIG. 4 shows a UV/VIS absorption spectrum of a reaction mixture having a toluenediamine $H_2O$ matrix which has been influenced by a gas bubble. The deviation of the "gas bubble spectrum" denoted by G from the expected aminonitrotoluene and dinitrotoluene spectra is sufficiently large for such a measured spectrum to be identified (for example by means of appropriate software) as not being usable for the concentration determination.

FIG. 5 shows a comparison of aminonitrotoluene and dinitrotoluene absorption spectra (ANT and DNT) with an absorption spectrum falsified by a gas bubble, denoted by G. The spectra can be clearly distinguished and the "gas bubble spectrum" can thus be recognized unambiguously.

FIG. 6 shows the concentration monitoring of the abovementioned pilot reactor in the hydrogenation of dinitrotoluene by measurement of the absorption of radiation having a wavelength of 500 nm by the reaction mixture. The absorption (absorbance) is plotted on the Y axis and the time in hours is plotted on the X axis. The first measurement cell (directly beyond the membrane filler) was located in a region having a pressure of from 20 to 25 bar, and the second measurement cell was located in a region of ambient pressure. The measured absorption signals for the two cells (cf. FIG. 6) were virtually identical. In this reactor, the catalyst was added discontinuously. As soon as deactivation of the catalyst has occurred (for example as a result of tar deposits on the catalyst surface), an increase in the absorption at 500 nm can be observed, with the increase being exponential (as observed between the 10th 12th hours). It is then possible either to reduce the inflow of dinitrotoluene (as carried out in hour 8.5) or to add new catalyst (as carried out in hour 11.5). FIG. 6 shows that the process of the invention makes possible reliable on-line monitoring of the hydrogenation of dinitrotoluene to toluenediamine by means of UV/VIS absorption measurements. In this way, the safety can be increased even in large industrial reactors. Furthermore, the catalyst consumption can be reduced and the deactivation of catalysts may also be able to be slowed.

The invention claimed is:

1. A process for the preparation of aromatic amines by hydrogenation of nitroaromatics or of aliphatic amino alcohols by hydrogenation of nitro alcohols comprising hydrogenating nitroaromatics or nitro alcohols in the presence of catalysts, wherein a fluid reaction mixture which comprises amines or amino alcohols is formed in a reactor and from which reaction mixture the catalysts are separated off, wherein, after the catalysts have been separated off, a measurement of the absorption of UV/VIS radiation by the reaction mixture is carried out to determine the concentration of nitro and nitroso compounds in the reaction mixture.

2. The process according to claim 1, wherein an absorption spectrum is measured in a wavelength range of the UV/VIS radiation or the absorption of UV/VIS radiation having a single wavelength is measured to determine the concentration of the nitro and nitroso compounds.

3. The process according to claim 2, wherein a measurement of the absorption of UV/VIS radiation by the reaction mixture is additionally carried out in a further wavelength range or at a further wavelength for the purposes of baseline correction.

4. The process according to claim 1, wherein the catalysts are separated off from the reaction mixture by means of at least one separation process selected from the group consisting of membrane filtration, sedimentation and centrifugation.

5. The process according to claim 1, wherein the measurement of the absorption of UV/VIS radiation is carried out at a pressure above ambient pressure or at ambient pressure.

6. The process according to claim 1, wherein an amount of nitroaromatics or catalysts fed to the reactor is regulated as a function of the determination of the concentration of the nitro and nitroso compounds in the reaction mixture.

7. The process according to claim 1, wherein aromatic amines are prepared by hydrogenation of nitroaromatics having one or more nitro groups and from 6 to 18 carbon atoms or aliphatic amino alcohols are prepared by hydrogenation of nitro alcohols.

8. The process according to claim 1, wherein toluenediamine is prepared by hydrogenation of dinitrotoluene and a measurement of the absorption of UV/VIS radiation is carried out to determine the concentration of essentially dinitrotoluene and aminonitrotoluene comprised in the reaction mixture.

9. The process according to claim 8, wherein the measurement of the absorption is carried out at a wavelength in the range from 450 to 550 nm or an absorption spectrum is recorded in a wavelength range from 350 to 750 nm.

10. The process according to claim 1, wherein said measurement of the absorption is carried out in a main stream.

11. The process according to claim 10, wherein said measurement of the absorption is carried out in a substream branched off from a main stream.

12. The process according to claim 1, wherein said process is for the preparation of aromatic amines and wherein said nitroaromatics are at least one nitroaromatic selected from the group consisting of nitrobenzene, 1,2-dinitrobenzene, 1,3-dinitrobenzene, 1,4-dinitrobenzene, o-nitrotoluene, m-nitrotoluene, p-nitrotoluene, 2,4-dinitrotoluene, 2,6-dinitrotoluene, 2,3-dinitrotoluene, 3,4-dinitrotoluene, 2,5-dinitrotoluene, 2,4,6-trinitrotoluene, 1,2-dimethyl-3-nitrobenzene, 1,2-dimethyl-4-nitrobenzene, 1,4-dimethyl-2-nitrobenzene, 1,3-dimethyl-2-nitrobenzene, 2,4-dimethyl-1-nitrobenzene, 1,3-dimethyl-5-nitrobenzene, 1-nitronaphthalene, 2-nitronaphthalene, 1,5-dinitronaphthalene, 1,8-dinitronaphthalene, 2-chloro-1,3-dinitrobenzene, 1-chloro-2,4-dinitrobenzene, o-chloronitrobenzene, m-chloronitrobenzene, p-chloronitrobenzene, 1,2-dichloro-4-nitrobenzene, 1,4-dichloro-2-nitrobenzene, 2,4-dichloro-1-nitrobenzene, 1,2-dichloro-3-nitrobenzene, 4-chloro-2-chloronitrotoluene, 4-chloro-3-chloronitrotoluene, 2-chloro-4-chloronitrotoluene, 2-chloro-6-nitrotoluene, o-nitroaniline, m-nitroaniline, p-nitroaniline and mixtures thereof.

13. The process according to claim 1, wherein said process is for the preparation of aliphatic aminoalcohols and wherein said nitroalcohol are at least one nitroalcohol selected from the group consisting of tri(hydroxymethyl)nitromethane, 2-nitro-2-methyl-propanediol, 2-nitro-2-ethyl-1,3-propanediol, 2-nitro-1-butanol, 2-nitro-2-methyl-1-propanol and mixtures thereof.

* * * * *